US008957048B2

(12) United States Patent
Vehige et al.

(10) Patent No.: US 8,957,048 B2
(45) Date of Patent: Feb. 17, 2015

(54) COMPOSITIONS FOR THE TREATMENT OF DRY EYE

(71) Applicant: Allergan, Inc., Irvine, CA (US)

(72) Inventors: Joseph G. Vehige, Laguna Niguel, CA (US); Peter A. Simmons, Yorba Linda, CA (US)

(73) Assignee: Allergan, Inc., Irvine, CA (US)

( * ) Notice: Subject to any disclaimer, the term of this patent is extended or adjusted under 35 U.S.C. 154(b) by 191 days.

(21) Appl. No.: 13/645,035

(22) Filed: Oct. 4, 2012

(65) Prior Publication Data

US 2013/0090308 A1   Apr. 11, 2013

Related U.S. Application Data

(60) Provisional application No. 61/544,151, filed on Oct. 6, 2011.

(51) Int. Cl.
| | | |
|---|---|---|
| *A61K 47/10* | (2006.01) |
| *A61K 47/26* | (2006.01) |
| *A61K 31/205* | (2006.01) |
| *A61K 33/22* | (2006.01) |
| *A61K 36/47* | (2006.01) |
| *A61K 31/745* | (2006.01) |
| *A61K 9/00* | (2006.01) |
| *A61K 47/32* | (2006.01) |
| *A61K 47/38* | (2006.01) |
| *A61K 31/047* | (2006.01) |
| *A61K 31/34* | (2006.01) |
| *A61K 31/717* | (2006.01) |

(52) U.S. Cl.
CPC ............ *A61K 31/745* (2013.01); *A61K 9/0048* (2013.01); *A61K 47/10* (2013.01); *A61K 47/26* (2013.01); *A61K 47/32* (2013.01); *A61K 47/38* (2013.01); *A61K 31/205* (2013.01); *A61K 33/22* (2013.01); *A61K 36/47* (2013.01); *A61K 31/047* (2013.01); *A61K 31/34* (2013.01); *A61K 31/717* (2013.01)
USPC .......................................................... 514/57

(58) Field of Classification Search
CPC ..... A61K 9/0048; A61K 47/10; A61K 47/26; A61K 31/205; A61K 33/22; A61K 36/47; A61K 2300/00
USPC .......................................................... 514/57
See application file for complete search history.

(56) References Cited

U.S. PATENT DOCUMENTS

| | | | |
|---|---|---|---|
| 4,201,706 A | 5/1980 | Trager |
| 5,145,871 A | 9/1992 | Cavazza |
| 5,432,199 A | 7/1995 | Cavazza |
| 5,527,831 A | 6/1996 | Franz |
| 5,827,512 A | 10/1998 | Gleich |
| 6,156,293 A | 12/2000 | Jutila |
| 6,193,957 B1 | 2/2001 | Ahmed |
| 6,228,392 B1 | 5/2001 | Morcos |
| 6,365,622 B1 | 4/2002 | Cavazza |
| 6,555,526 B2 | 4/2003 | Matsuo |
| 6,585,987 B1 | 7/2003 | Fransoni |
| 7,045,121 B2 | 5/2006 | Chang |
| 8,496,976 B2 * | 7/2013 | Gore et al. ............... 424/725 |
| 2002/0071874 A1 | 6/2002 | Olejnik |
| 2004/0192647 A1 | 9/2004 | Babizhayev |
| 2005/0009836 A1 | 1/2005 | Laskar |
| 2006/0035842 A1 | 2/2006 | Tsuzuki |
| 2006/0106104 A1 | 5/2006 | Vehige |

FOREIGN PATENT DOCUMENTS

| | | |
|---|---|---|
| EP | 0436726 | 7/1990 |
| EP | 0778021 | 6/1997 |
| JP | 2010-036255 | 2/2010 |
| WO | 98-41208 | 9/1998 |
| WO | 02-38161 | 5/2002 |
| WO | 03-051332 | 6/2003 |
| WO | 2004-084877 | 7/2004 |
| WO | 2010-047927 | 4/2010 |
| WO | 2010-141648 | 12/2010 |

OTHER PUBLICATIONS

Glossary of medical education terms, Institute of International Medical Education. http://www.iime.org/glossary.htm Accessed in Mar. 2013.*
Javadi et al. Dry eye syndrome. J Ophthalmic Vis Res 6:192-198, 2011.*
Albietz, Julie et al, A Comparison of the Effect of Refresh plus and Bion Tears on Dry Eye Symptoms and Ocular Surface Health in Myopic LASIK Patients, the CLAO Journal, 2002, 96-100, 28(2).
Alfieri, Roberta et al, Compatible Osmolytes Modulate the Response of Porcine Endothelial Cells to Hypertonicity and Protect Them From Apoptosis, J. Physiol., 2002, 499-508, 540.
Barker, Robert et al, Acidic Polyamino Acids Inhibit Human Eosinophil Granule Major Basic Protein Toxicity. Evidence of a Functional Role for ProMBP, J. Clin. Invest., Sep. 1991, 798-805, 88.
Biocompare® : Product Review: Upstate's Beadlyte Human/Mouse Cytokine Detection Kits, 6115/2004, 3 Pages.
Brown, Theodore et al, Glossary: Salt, Chemistry: The Central Science, 2006, G-10, 10th Edition.
Burg, Maurice, Molecular Basis of Osmotic Regulation, American Physiological Society, 1995, F983-F996, 268.
Cammarata, Patrick et al, Osmoregulatory Alterations in taurine Uptake by Cultured Human and Bovine lens Epithelial Cells, Invest. Ophthalmol. Vis. Sci., 2002, 425-433, 43.
Gilbard, Jeffrey, Tear Film Osmolarity and Keratoconjunctivitis Sicca, the CLAO Journal, Jul. 1985, 243-250, 11 (3).

(Continued)

*Primary Examiner* — Brandon Fetterolf
*Assistant Examiner* — Yih-Horng Shiao
(74) *Attorney, Agent, or Firm* — Mark D. Kafka

(57) ABSTRACT

The present invention relates to ophthalmic compositions and methods useful to treat dry eye, or to diagnose, cure, mitigate, treat, or prevent dry eye syndrome in man or other animals.

20 Claims, No Drawings

(56) References Cited

OTHER PUBLICATIONS

Matsuo, Toshihiko et al, Trehalose Eye Drops in the Treatment of Dry Eye Syndrome, Ophthalmology, 2002, 2024-2029, 109.

McGrogan, Michael et al, Isolation of a Complementary DNA Clone Encoding a Precursor to Human Eosinophil Major Basic Protein, J. Exp. Med., Dec. 1988, 2295-2308, 168.

Nakajima, Toshiharu et al, Gene Expression Screening of Human Mast Cells and Eosinophils Using High-Density Oligonucleotide Probe Arrays: Abundant Expression of Major Basic Protein in Mast Cells, Blood, Aug. 2001, 1127-1134, 98 (4).

Peluso, Gianfranco et al, Carnitine: An Osmolyte That Plays a Metabolic Role, Journal of Cellular Biochemistry, 2000, 1-10, 80.

Pessotto, P. et al, The Presence of L-Carnitine in Ocular Tissues of the Rabbit, Journal of Ocular Pharmacology, 1994, 643-651, 10 (4).

Popken-Harris, Pamela et al, Biochemical Properties, Activities, and Presence in Biologic Fluids of Eosinophil Granule Major Basic Protein, J. Allergy Clin. Immunol., 1994, 1282-1289, 94 (6).

Popken-Harris, Pamela et al, Regulation and Processing of a Precursor Form of Eosinophil Granule Major Basic Protein (ProMBP) in Differentiating Eosinophils, Blood, Jul. 1998, 623-631, 92 (2).

Rhyne, P.W. et al, Analysis of Apoptotic Cells Using Beadlyte Suspension Arrays, Biotechniques, Sep. 2003, 624-629 (Abstract), 35 (3).

Shioda, Ryo et al, Osmosensitive Taurine Transporter Expression and Activity in Human Corneal Epithelial Cells, Investigative Ophthalmology & Visual Science, Sep. 2002, 2916-2922, 43 (9).

Voet, Donald et al, Transport Across the Mitochondrial Membrane, Biochemistry, 1990, 622.

Patent Cooperation Treaty, Notification of Transmittal of the International Search Report and the Written Opinion of the International Searching Authority, or the Declaration, Form PCT/ISA/220, Int. App. No. PCT/US2012/058893, Dec. 3, 2012.

* cited by examiner

COMPOSITIONS FOR THE TREATMENT OF DRY EYE

CROSS REFERENCE

This application claims the benefit of U.S. Provisional Patent Application Ser. No. 61/544,151, filed on Oct. 6, 2011, the entire disclosure of which is incorporated herein by this specific reference.

BACKGROUND OF THE INVENTION

1. Field of the Invention

The present invention relates to ophthalmic compositions and methods useful to treat dry eye, or to diagnose, cure, mitigate, treat, or prevent dry eye syndrome in man or other animals.

2. Background of the Art

Dry eye is a multifactorial disease of the tears and ocular surface that results in symptoms of discomfort, visual disturbance, and tears film instability with potential damage to the ocular surface. The normal tear film is a relatively stable, thin film composed of a superficial lipid layer and an aqueous layer intermixed with a mucus gel layer which is partially adherent to the corneal and conjunctival surface epithelium. Natural tear film is important for the lubrication and maintenance of the refractive surface of the eye. Dry eye syndrome is a complex disease characterized by a dysfunction of one or more components of the tear film, leading to the loss of tear film stability, a hyperosmotic shift in the tear film osmotic balance, and/or an inadequate amount of fluid on the ocular surface. This is characterized by rapid break-up of the tear film and numerous symptoms, including burning/stinging, foreign body sensation, itching, and photophobia. The majority of patients with dry eye syndrome are prescribed or recommended artificial tears. Also recommended are lid compresses and scrubs, and addition of essential fatty acids to the diet.

Dry Eye Syndrome is a common disorder of the normal tear film that results from one of the following: decreased tear production, excessive tear evaporation, an abnormality in the production of mucus or lipids normally found in the tear layer.

Aqueous (watery) tear deficiency is caused by either poor production of watery tears or excessive evaporation of the watery tear layer.

Poor production of tears by the tear glands may be a result of age, hormonal changes, or various autoimmune diseases, such as primary Sjogren syndrome, rheumatoid arthritis, or lupus.

Evaporative loss of the watery tear layer is usually a result of an insufficient overlying lipid layer. Some medications, such as antihistamines, antidepressants, beta-blockers, and oral contraceptives, may decrease tear production. If blinking is decreased or if the eyelids cannot be closed, the eyes may dry out because of tear evaporation.

Reading, watching TV, or performing a task that requires close attention with the eyes, may decrease the blinking, allowing excessive evaporation of the tears.

LASIK and other vision correction procedures can cause dry eyes after they penetrate the eye's surface and reduce corneal nerve sensitivity. Afterwards the eye fails to sense the need for lubrication and inadequate tear production results. New ophthalmic compositions for treating eyes and methods of treating dry eyes have been discovered.

SUMMARY OF THE INVENTION

It has now been discovered novel ophthalmic compositions for treating dry eye syndrome, which may include a combination of a demulcent or film forming material and a tonicity agent. These compositions may be used to treat dry eye, or to diagnose, cure, mitigate, treat, or prevent dry eye syndrome in man or other animals. These formulations are sterile, buffered, oil and water emulsion artificial tear products formulated for the relief of ocular surface irritation and symptoms of dryness.

These compositions are typically ophthalmically acceptable liquids. An ophthalmically acceptable liquid includes a liquid formulated that is tolerable to a patient for topical ophthalmic use. Additionally, an ophthalmically acceptable liquid could either be packaged for single use, or for multiple uses containing a preservative to prevent contamination.

For ophthalmic application, solutions or medicaments may be prepared using a physiological saline solution as a major vehicle. Ophthalmic solutions may be maintained at a comfortable pH with an appropriate buffer system. The formulations may also contain conventional, pharmaceutically acceptable preservatives, stabilizers and surfactants.

An ophthalmically acceptable liquid may include demulcents or film forming materials. Examples of demulcents may include, but are not limited to polymers such as polyvinyl alcohol, povidone, hydroxypropyl methyl cellulose, poloxamers, carboxymethyl cellulose, hydroxyethyl cellulose, acrylates; surfactants such as polyoxyethylene (20) sorbitan monooleate and glycerin. The amount of demulcent may vary. In some embodiments, the amount of any demulcent such as those listed above may be from about 0.1% w/w to about 2% w/w, or from about 0.3% w/w to about 0.7% w/w, or from about 0.3% w/w to about 0.5% w/w, or about 0.5% w/w.

An ophthalmically acceptable liquid may include a buffer. The buffer may vary, and may include any weak conjugate acid-base pair suitable for maintaining a desirable pH range. Examples include, but are not limited to, acetate buffers, citrate buffers, phosphate buffers, borate buffers, or a combination thereof. Acids or bases may be used to adjust the pH of these formulations as needed. The amount of buffer used may vary. In some embodiments, the buffer may have a concentration in a range of about 1 nM to about 100 mM. The pH of a buffered solution may be increased by the addition of sodium hydroxide or another base, or decreased by the addition of hydrochloric acid or another acid. In some embodiments, the pH of a composition may be from about 7 to about 7.5, or from about 7.2 to about 7.4, or about 7.3.

An ophthalmically acceptable liquid may include a preservative. The preservative may vary, and may include any compound or substance suitable for preventing microbial contamination in an ophthalmic liquid subject to multiple uses from the same container. Preservatives that may be used in the pharmaceutical compositions disclosed herein include, but are not limited to, cationic preservatives such as quaternary ammonium compounds including benzalkonium chloride, polyquad, and the like; guanidine-based preservatives including polyhexamethylene biguanide (PHMB), chlorhexidine, and the like; chlorobutanol; mercury preservatives such as thimerosal, phenylmercuric acetate and phenylmercuric nitrate; and oxidizing preservatives such as stabilized oxychloro complexes (e.g. Purite®). Purite® is a registered trademark of Allergan, Inc.

In some embodiments, the amount of preservative in the liquid may be from about 0.0001% w/w to about 25% w/w, or from about 0.002% w/w to about 0.05% w/w, or from about 0.005% w/w to about 0.02% w/w, or about 0.01% w/w.

An ophthalmically acceptable liquid may include a surfactant. The surfactant may vary, and may include any compound that is surface active or can form micelles. A surfactant may be used for assisting in dissolving an excipient or an active agent, dispersing a solid or liquid in a composition, enhancing wetting, modifying drop size, stabilizing an emulsion, or a number of other purposes. Useful surfactants include, but are not limited to, surfactants of the following classes: alcohols; amine oxides; block polymers; carboxylated alcohol or alkylphenol ethoxylates; carboxylic acids/fatty acids; ethoxylated alcohols; ethoxylated alkylphenols; ethoxylated arylphenols; ethoxylated fatty acids; ethoxylated fatty esters or oils (animal and vegetable); fatty esters; fatty acid methyl ester ethoxylates; glycerol esters; glycol esters; lanolin-based derivatives; lecithin and lecithin derivatives; lignin and lignin derivatives; methyl esters; monoglycerides and derivatives; polyethylene glycols; polymeric surfactants; propoxylated and ethoxylated fatty acids, alcohols, or alkyl phenols; protein-based surfactants; sarcosine derivatives; sorbitan derivatives; sucrose and glucose esters and derivatives. In some embodiments, the surfactant may include polyethylene glycol (15)-hydroxystearate (CAS Number 70142-34-6, available as Solutol HS 15® from BASF), polyoxyethylene-polyoxypropylene block copolymer (CAS No. 9003-11-6, available as Pluronic® F-68 from BASF), polyoxyethylene 40 stearate (POE40 stearate), polysorbate 80 or polyoxyethylene (20) sorbitan monooleate (CAS No. 9005-65-6), sorbitan monostearate (CAS No. 1338-41-6, available as Span™ 60 from Croda International PLC), polyoxyethylenglyceroltriricinoleat 35 (CAS No. 61791-12-6, available as Cremophor EL® from BASF). The amount of surfactant may vary. In some embodiments, the amount of any surfactant such as those listed above may be from about 0.001% w/w to about 5% w/w, or from about 0.1% w/w to about 2 w/w %, or from about 0.3% to about 0.7%, or from about 0.3% w/w to about 0.5% w/w, or from about 0.1% w/w to about 1% w/w, or about 0.5% w/w.

An ophthalmically acceptable liquid may include a stabilizer. Examples of suitable stabilizers include, but are not limited to, polyvinyl alcohol, povidone, hydroxypropyl methyl cellulose, poloxamers, carboxymethyl cellulose, hydroxyethyl cellulose, and acrylates such as acrylates/C10-30 alkyl acrylate crosspolymer (e.g. Pemulen™ Pemulen™ TR-2). Acrylates/C10-30 alkyl acrylate crosspolymer is sold and is known as Pemulen™ TR-2. In some embodiments, the amount of stabilizer may be from about 0.01% to about 1%, or from about 0.1% w/w to about 1% w/w, or about 0.1% w/w.

An ophthalmically acceptable liquid may include a tonicity agent. The tonicity agent may vary, and may include any compound or substance useful for adjusting the tonicity of an ophthalmic liquid. Examples include, but are not limited to, salts, particularly sodium chloride, potassium chloride, mannitol and glycerin, or any other suitable ophthalmically acceptable tonicity adjustor. The amount of tonicity agent may vary depending upon whether an isotonic, hypertonic, or hypotonic liquid is desired. In some embodiments, the amount of a tonicity agent such as those listed above may be at least from about 0.0001% w/w to about 5% w/w, or from about 0.2% to about 5% w/w, or from about 0.5% w/w to about 2% w/w, or about 1.0% w/w.

An ophthalmically acceptable liquid may include an antioxidant. The antioxidant may vary, and may include any compound or substance that is useful in reducing oxidation of any compound present in an ophthalmically acceptable liquid. Examples, not limited to, are: sodium metabisulfite, sodium thiosulfate, acetylcysteine, butylated hydroxyanisole, and butylated hydroxytoluene.

An ophthalmically acceptable liquid may include a chelating agent. The chelating agent may vary, and may include any compound or substance that is capable of chelating a metal. A useful chelating agent is edetate disodium, although other chelating agents may also be used in place or in conjunction with it.

Compositions may be aqueous solutions or emulsions, or some other acceptable liquid form. For an emulsion, one or more oils may be used to form the emulsion. Suitable oils include, but are not limited to anise oil, castor oil, clove oil, cassia oil, cinnamon oil, almond oil, corn oil, arachis oil, cottonseed oil, safflower oil, maize oil, linseed oil, rapeseed oil, soybean oil, olive oil, caraway oil, rosemary oil, peanut oil, peppermint oil, sunflower oil, eucalyptus oil, sesame oil, and the like. In some embodiments, the amount of oil such as those listed above may be from about 0.0001% w/w to about 5% w/w, or from about 0.005% w/w to about 1 w/w %, or from about 0.01% w/w to about 0.2 w/w %, or from about 0.05% w/w to about 0.5% w/w, or from about 0.2% w/w to about 5% w/w, or from about 0.5% w/w to about 2% w/w, or from about 0.1 to about 0.2%, or about 0.175% w/w, or about 0.075% w/w.

Other excipients may include erythritol, a carnitine, including L-carnitine (levocarnitine} or R-carnitine. In some embodiments, the amount of erythritol may be from about 0.05% to about 3% w/w, or from about 0.1% w/w to about 0.5% w/w, or about 0.25% w/w.

In some embodiments, the amount of levocarnitine may be from about 0.05% to about 3% w/w, or from about 0.1% w/w to about 0.5% w/w or about 0.25% w/w.

Table 1 includes a list of components that may be used in a dry eye composition.

TABLE 1

| Ingredient | Amount |
| --- | --- |
| Polyoxyethylene (20) sorbitan monooleate | omitted, or about 0.1-2%, about 0.3%-0.7%, or about 0.5% w/w |
| Carboxymethylcellulose sodium (low viscosity) | omitted, or about 0.1-2%, about 0.3%-0.7%, or about 0.5% w/w |
| Glycerin | omitted, or about 0.2-5%, about 0.5-2%, or about 1.0% w/w |
| Purite ® | omitted, or about 0.002%-0.05%, about 0.005%-0.02%, or about 0.01% w/w |
| Boric Acid | omitted, or about 0.02-2%, about 0.5-0.7%, or about 0.6% w/w |
| A C10-30 alkyl acrylate crosspolymer | omitted, or about 0.02-0.5%, about 0.05-0.2%, or about 0.1% w/w |
| Castor Oil | omitted, or about 0.05-0.5%, about 0.1-0.2%, or about 0.175% w/w |
| Olive Oil, Super Refined (non-preserved) | omitted, or about 0.005-1%, about 0.01-0.2%, or about 0.075% w/w |
| Erythritol | omitted, or about 0.05-3%, about 0.1-0.5%, or about 0.25% w/w |
| Levocarnitine | omitted, or about 0.05-3%, about 0.1-0.5%, or about 0.25% w/w |
| Sodium hydroxide | omitted, or add to pH of about 7-7.5, 7.2-7.4, or about 7.3. |
| Water | QS 100% w/w |

DETAILED DESCRIPTION OF THE INVENTION

Some embodiments of the invention comprise, or consist of, Polyoxyethylene (20) sorbitan monooleate, carboxymethylcellulose sodium (low viscosity), glycerin, Purite®, boric acid, an acrylates/C10-30 alkyl acrylate crosspolymer (Pemulen™ TR-2), castor oil, olive oil, erythritol, levocarnitine, sodium hydroxide, and water.

Some embodiments of the invention comprise, or consist of, Polyoxyethylene (20) sorbitan monooleate, carboxymethylcellulose sodium (low viscosity), glycerin, Purite®, boric acid, an acrylates/C10-30 alkyl acrylate crosspolymer (Pemulen™ TR-2), castor oil, erythritol, levocarnitine, sodium hydroxide, and water.

Some embodiments of the invention comprise, or consist of, Polyoxyethylene (20) sorbitan monooleate, carboxymethylcellulose sodium (low viscosity), glycerin, boric acid, an acrylates/C10-30 alkyl acrylate crosspolymer (Pemulen™ TR-2), castor oil, erythritol, levocarnitine, sodium hydroxide, and water.

Some embodiments of the invention comprise, or consist of polyoxyethylene (20) sorbitan monooleate, carboxymethylcellulose sodium, glycerin, boric acid, acrylates/C10-30 alkyl acrylate crosspolymer, castor oil, erythritol, levocarnitine, sodium hydroxide, and water.

Some embodiments of the invention comprise, or consist of polyoxyethylene (20) sorbitan monooleate, carboxymethylcellulose sodium, glycerin, boric acid, acrylates/C10-30 alkyl acrylate crosspolymer, stabilized oxychloro complexes, castor oil, erythritol, levocarnitine, sodium hydroxide, and water.

EXAMPLE 1

A formulation is prepared for use as an artificial tears product according to Table 2:

TABLE 2

| Ingredient | Amount |
| --- | --- |
| Polysorbate 80 | 0.5% w/w |
| Carboxymethylcellulose sodium (low viscosity) | 0.5% w/w |
| Glycerin | 1.0% w/w |
| Purite ® | 0.01% w/w |
| Boric Acid | 0.6% w/w |
| Pemulen ™ TR-2 | 0.1% w/w |
| Castor Oil | 0.175% w/w |
| Olive Oil, Super Refined (non-preserved) | 0.075% w/w |
| Erythritol | 0.25% w/w |
| Levocarnitine | 0.25% w/w |
| Sodium hydroxide | Add to pH 7.3 |
| Water | QS 100% w/w |

The formulation of Table 2 is administered to a person suffering from dry eye syndrome about 1-10 times per day for relief of dry eye symptoms.

EXAMPLE 2

A formulation is prepared for use as an artificial tears product according to Table 3:

TABLE 3

| Ingredient | Amount |
| --- | --- |
| Polysorbate 80 | 0.5% w/w |
| Carboxymethylcellulose sodium (low viscosity) | 0.5% w/w |
| Glycerin | 1.0% w/w |
| Purite ® | 0.01% w/w |
| Boric Acid | 0.6% w/w |
| Pemulen ™ TR-2 | 0.1% w/w |
| Castor Oil | 0.25% w/w |
| Erythritol | 0.25% w/w |
| Levocarnitine | 0.25% w/w |
| Sodium hydroxide | Add to pH 7.3 |
| Water | QS 100% w/w |

The formulation of Table 3 is administered to a person suffering from dry eye syndrome about 1-10 times per day for relief of dry eye symptoms.

Some embodiments of the present invention include:

1. An ophthalmic composition comprising polyoxyethylene (20) sorbitan monooleate, carboxymethylcellulose sodium, glycerin, boric acid, acrylates/C10-30 alkyl acrylate crosspolymer, castor oil, erythritol, levocarnitine, sodium hydroxide, and water.
2. The composition of paragraph 1, wherein the polyoxyethylene (20) sorbitan monooleate is present at a concentration of about 0.1% w/w to about 2% w/w.
3. The composition of paragraph 1 wherein the carboxymethylcellulose sodium is present at a concentration of about 0.1% w/w to about 2% w/w.
4. The composition of paragraph 1, wherein the glycerin is present at a concentration of about 0.2% w/w to about 5% w/w.
5. The composition of paragraph 1, wherein the boric acid is present at a concentration of about 0.02% to about 2% w/w.
6. The composition of paragraph 1, wherein the acrylates/C10-30 alkyl acrylate crosspolymer is present at a concentration of about 0.02% to about 0.5% w/w.
7. The composition of paragraph 1, wherein the castor oil is present at a concentration of about 0.05% to about 0.5% w/w.
8. The composition of paragraph 1, wherein the erythritol is present at a concentration of about 0.05% or about 3% w/w.
9. The composition of paragraph 1, wherein the levocarnitine is present at a concentration of about 0.05% to about 3% w/w.
10. The composition of paragraph 1, wherein the pH is about 7.3.
11. The composition of paragraph 1, comprising about 0.5% w/w polyoxyethylene (80) sorbitan monooleate, about 0.5% w/w carboxymethylcellulose sodium, about 1.0% w/w glycerin, about 0.6% w/w boric acid, about 0.1% w/w acrylates/C10-30 alkyl acrylate crosspolymer, about 0.25% w/w castor oil, about 0.25% w/w erythritol, about 0.25% w/w levocarnitine, sodium hydroxide, a pH of about 7.3 and water.
12. A method of treating, diagnosing, curing, mitigating or preventing dry eye syndrome comprising administering an effective amount of an ophthalmic composition according to paragraph 1 to an eye of a man or other animal in need thereof.
13. The method according to paragraph 12, wherein the ophthalmic composition comprises about 0.5% w/w polyoxyethylene (80) sorbitan monooleate, about 0.5% w/w carboxymethylcellulose sodium, about 1.0% w/w glycerin, about 0.6% w/w boric acid, about 0.1% w/w acrylates/C10-30 alkyl acrylate crosspolymer, about 0.25% w/w castor oil, about 0.25% w/w erythritol, about 0.25% w/w levocarnitine, sodium hydroxide, a pH of about 7.3 and water.
14. The composition of paragraph 1, further comprising stabilized oxychloro complexes.
15. The composition of paragraph 14, wherein the stabilized oxychloro complex is present at a concentration of about 0.002% or about 0.05% w/w.
16. The ophthalmic composition of paragraph 11, further comprising about 0.01% w/w of stabilized oxychloro complex.
17. A method of treating, diagnosing, curing, mitigating or preventing dry eye syndrome comprising administering an effective amount of an ophthalmic composition according to paragraph 14 to an eye of a man or other animal in need thereof.
18. The method according to paragraph 17, wherein the ophthalmic composition comprises about 0.5% w/w polyoxyethylene (20) sorbitan monooleate, about 0.5% w/w carboxymethylcellulose sodium, about 1.0% w/w glycerin, about 0.01% w/w of stabilized oxychloro complexes, about 0.6% w/w boric acid, about 0.1% w/w acrylates/C10-30 alkyl acrylate crosspolymer, about 0.25% w/w Castor Oil, about 0.25% w/w erythritol, about 0.25% w/w levocarnitine, sodium hydroxide to obtain a pH of about 7.3 and water.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained. At the very least, and not as an attempt to limit the application of the doctrine of equivalents to the scope of the claims, each numerical parameter should at least be construed in light of the number of reported significant digits and by applying ordinary rounding techniques.

The terms "a," "an," "the" and similar referents used in the context of describing the invention (especially in the context of the following claims) are to be construed to cover both the singular and the plural, unless otherwise indicated herein or clearly contradicted by context. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of any claim. No language in the specification should be construed as indicating any non-claimed element essential to the practice of the invention.

Groupings of alternative elements or embodiments disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments are described herein, including the best mode known to the inventors for carrying out the invention. Of course, variations on these described embodiments will become apparent to those of ordinary skill in the art upon reading the foregoing description. Accordingly, the claims include all modifications and equivalents of the subject matter recited in the claims as permitted by applicable law. Moreover, any combination of the above-described elements in all possible variations thereof is contemplated unless otherwise indicated herein or otherwise clearly contradicted by context.

Clinical Aspects:

A completed clinical study had for objective to evaluate the safety, efficacy and acceptability of the two candidates: Formulation A and Formulation B in comparison with Allergan's existing OPTIVE™ Eye drops in subjects with signs and symptoms of dry eye disease.

The results showed that Formulation A and Formulation B are clinically safe and effective in subjects with signs and symptoms of dry eye disease.

Formulation A is a multidose (MD) formulation containing polysorbate 80, carboxymethylcellulose sodium, glycerin, Purite®, boric acid, Pemulen™ TR-2, castor oil, erythritol, levocarnitine, sodium hydroxide, and purified water for injection, supplied in 15 ml multidose bottles. The solution is clinically safe and effective in subjects with signs and symptoms of dry eye disease.

Formulation B is an unit-dose (UD) formulation containing polysorbate 80, carboxymethylcellulose sodium, glycerin, boric acid, Pemulen™ TR-2, castor oil, erythritol, levocarnitine, sodium hydroxide, and purified water for injection, supplied in 0.4 ml unit-dose vials. This solution is clinically safe and effective in subjects with signs and symptoms of dry eye disease.

The study was a multicenter, investigator-masked, randomized, active-controlled, 4-arm, parallel group study designed to compare the safety, efficacy, and acceptability of Formulation A to OPTIVE™ Lubricant Eye Drops Multidose (OPTIVE MD) and Formulation B to OPTIVE™ Sensitive Preservative-free Lubricant Eye Drops Unit-dose (OPTIVE UD).

Control solution OPTIVE™ Lubricant Eye Drops Multidose (OPTIVE MD) contained carboxymethylcellulose sodium, glycerin, boric acid, sodium borate, sodium citrate, potassium chloride, levocarnitine, erythrol, calcium chloride, magnesium chloride, Purite®, purified water and sodium hydroxide to adjust pH to 7.3, supplied in 15 ml multidose bottles.

Control solution OPTIVE™ Sensitive Preservative-free Lubricant Eye Drops Unit-dose (OPTIVE UD) contained carboxymethylcellulose sodium, glycerin, boric acid, sodium borate, sodium citrate, potassium chloride, levocarnitine, erythrol, calcium chloride, magnesium chloride, purified water for injection and sodium hydroxide to adjust pH to 7.3, supplied in 0.4 ml unit-dose vials.

The duration of the study was 30 days for each subject and consisted of up to 3 scheduled visits (day 1 [baseline], day 7, and day 30 [exit]). On day 1, eligible subjects with signs and symptoms of dry eye disease were assigned according to a 2:2:1:1 treatment allocation ratio to use Formulation A, OPTIVE MD, Formulation B, or OPTIVE UD, respectively.

Approximately 300 subjects were enrolled at 13 to 14 sites within the USA in order to have 288 completed subjects assuming a dropout rate of approximately 5%. For enrollment into the study, each subject had to meet certain inclusion criteria and none of the exclusion criteria.

Subjects were instructed to instill 1 to 2 drops of their assigned study product in each eye, as needed, but at least 2 times daily for 30 days. Subjects could have voluntarily withdrawn from the study at any time. Additionally, subjects could have been discontinued from the study by an investigator for reasons such as adverse events, loss to follow-up, protocol violations, or lack of efficacy.

Subjects randomized to Formulation A, OPTIVE MD received kits containing 2 multidose bottles (15 mL in each bottle) of study product, and were instructed to use 1 bottle until it was empty and then to use the second bottle.

Subjects randomized to Formulation B and OPTIVE UD received kits containing 180 unit-dose vials (0.4 mL in each vial) of study product, and were instructed to use 1 vial per dosing for both eyes.

Each subject was instructed to instill 1 to 2 drops of study product in each eye, as needed, but at least 2 times daily for the entire duration of the study (from day 1 after randomization through day 30, prior to exiting the study).

Subjects and all investigative site staff were masked to the study treatment. To maintain product masking, both the Formulation B and the OPTIVE UD drops were provided in identical 0.4 mL unit-dose vials while the Formulation A and the OPTIVE MD drops were provided in identical 15 mL multidose bottles.

Primary Efficacy Measurements:

The primary efficacy measure was the Ocular Surface Disease Index© (OSDI) Questionnaire at day 30 in the intent-to-treat (ITT) population. The OSDI Questionnaire consisted of 12 questions with a 5-point scale (0=none of the time; 1=some of the time; 2=half of the time; 3=most of the time; 4=all of the time; some questions had a possible "N/A" [not applicable] response) (Schiffman et al, 2000). Subjects were asked to evaluate the frequency of various symptoms, related visual functions, and environmental triggers of dry eye using the 5-point scale. Subjects were asked to base their evaluation on the frequency of their symptoms over the last week before the study visit. This was evaluated overall, not per eye.

The primary efficacy analysis was performed on the change from baseline in OSDI score at day 30 via a 2-way analysis of variance (ANOVA) model with treatment and baseline OSDI stratification as the main effects. Last observation carried forward (LOCF) was used to impute missing data. Noninferiority was tested using a 2-sided confidence interval (CI). The treatment difference and 95% CI in change from baseline in OSDI score at day 30 between Formulation B and OPTIVE UD (Formulation B minus OPTIVE UD) were calculated based on the ANOVA model. Non-inferiority was established if the upper limit of the 95% CI was less than the prespecified margin of 7.3. The primary efficacy endpoint was met. At day 30, no statistically significant difference was observed between the Formulation B and the OPTIVE UD groups in the mean change from baseline in OSDI score (95% confidence interval [−5.42, 2.51]), in the ITT population. The Formulation B was noninferior to the OPTIVE UD formulation in reducing the severity of symptoms of dryness as measured by the change from baseline in OSDI score.

Similar to the ITT population, there was no statistically significant difference between the Formulation B and OPTIVE UD groups of the per-protocol (PP) population in the mean change from baseline in OSDI score at day 30. The 95% confidence interval at the day 30 visit was (−5.72, 2.37); with an upper limit that is lower than the clinically relevant margin of 7.3.

In all 4 treatment groups, there was a statistically significant difference ($p < 0.001$) in the mean change from baseline in OSDI score at the day 7 and day 30 visits for both the ITT and the PP population.

The Formulation B group was noninferior to the Formulation A group in the mean change from baseline in OSDI score at day 30.

Overall, there were no statistically significant differences between the Formulation B and OPTIVE UD groups, Formulation B and Formulation A groups, or Formulation A and OPTIVE MD groups.

Efficacy:

The results of this study demonstrate that Formulation B is noninferior to the OPTIVE UD formulation in reducing the severity of symptoms of dryness in subjects with mild to severe dry eye.

Safety:

Formulation B appeared to be well tolerated during the study. Throughout the study, there were no treatment-related serious adverse events. The safety profile was consistent with OPTIVE UD, OPTIVE MD, and Formulation A. This is supportive of the safety of the Formulation B in clinical use, and confirms the safety of the Formulation A.

Secondary Efficacy Measurements:

The Secondary efficacy measures included (tear break-up time) TBUT, corneal staining, conjunctival staining, and Schirmer test.

TBUT was measured (in seconds) 3 times in each eye during the 2 minute wait for corneal staining. Fluorescein supplied for the study was applied onto the superior bulbar conjunctiva. This 1 instillation of sodium fluorescein was used for TBUT and corneal staining. However, if needed, the fluorescein could have been reapplied for the corneal staining after the TBUT. The examination was performed with the slit lamp at 10× magnification using cobalt blue illumination and the yellow barrier filter. Three consecutive TBUTs were performed in each eye and all 3 measurements were timed with the stopwatch provided.

The Schirmer Test (with Anesthesia) was performed in each eye after all other ophthalmic testing. One drop of anesthetic was instilled and the test begun precisely 4 minutes after instillation. The test was conducted in a dimly lit room. While the subject looked upward, the lower lid was gently drawn downward and temporally. The rounded bent end of the sterile strip was hooked in the lower conjunctival sac over the junction of the temporal and central one-third of the lower eyelid margin in each eye. After 5 minutes, the tear front was marked and measured on each of the sterile strips.

The raw values of these measures were summarized for the ITT population, with missing data imputation using LOCF at each scheduled follow-up visit. The treatment difference and 95% CI for between-treatment comparisons were calculated. The treatment differences and 95% CIs in change from baseline in OSDI score at day 30 between Formulation B and Formulation A, Formulation A and OPTIVE MD were also analyzed as secondary efficacy variables.

The Formulation B group was noninferior to the OPTIVE UD and Formulation A groups in the secondary efficacy measures of TBUT, corneal staining, conjunctival staining, and Schirmer test.

Efficacy Conclusions:

The objective of the current study was to evaluate the safety, efficacy and acceptability of the Formulation B in subjects with signs and symptoms of dry eye disease. The study was performed to compare the Formulation B to existing OPTIVE UD formulation and also to the Formulation A. The primary efficacy endpoint was met in this study.

There was no difference between the Formulation B group and the control OPTIVE UD group in the mean change from baseline in OSDI score at day 30. The Formulation B formulation was noninferior to OPTIVE UD and Formulation A in reducing the severity of symptoms of dryness as measured by the OSDI questionnaire. Although there were statistically significant differences between the Formulation B and Formulation A group in the overall analyses and subgroup analyses (by OSDI stratum) of the primary efficacy measure, favoring the Formulation B group, the study was not designed to test statistical superiority between the two groups, therefore firm conclusions regarding the superiority of Formulation B versus Formulation A cannot be made. Since this was a 4-arm study, efficacy comparisons between the Formulation A and OPTIVE MD formulations were also performed. Overall there was no difference in efficacy between the Formulation A and OPTIVE MD formulations.

The Formulation B formulation appeared to have an acceptable safety profile.

Efficacy: The results of this study demonstrate that the Formulation B formulation is noninferior to the OPTIVE UD formulation in reducing the severity of symptoms of dryness in subjects with mild to severe dry eye.

In a different study, it has been shown that Formulation B reduces evaporation of tears, helping therefore the tear film stability and protecting the tear film osmotic balance in case a hyperosmotic shift should occur. Formulation B reduced evaporation in subjects with and without dry eye syndrome.

The following non-limiting examples illustrate further certain aspects of the present invention:

EXAMPLE 3

Eye drops of Formulation B, are administered to the eye of a patient, Caucasian 52 year old male, complaining about dry eyes. After applying the eye drops twice daily in each eye for two days the patient has relief from dry eye symptoms.

EXAMPLE 4

A drop of Formulation A is administered to the each eye of a person suffering from dry eye, one to three times a day. After two days the person feels relief from the dry eye symptoms.

It is to be understood that the embodiments disclosed herein are illustrative of the principles of the claims. Other modifications that may be employed are within the scope of the claims. Thus, by way of example, but not of limitation, alternative embodiments may be utilized in accordance with the teachings herein. Accordingly, the claims are not limited to embodiments precisely as shown and described.

What is claimed is:

1. An ophthalmic composition consisting of polyoxyethylene (20) sorbitan monooleate, carboxymethylcellulose sodium, glycerin, boric acid, acrylates/C10-30 alkyl acrylate crosspolymer, castor oil, erythritol, levocarnitine, sodium hydroxide, and water.

2. The composition of claim 1, wherein the polyoxyethylene (20) sorbitan monooleate is present at a concentration of about 0.1% w/w to about 2% w/w.

3. The composition of claim 1 wherein the carboxymethylcellulose sodium is present at a concentration of about 0.1% w/w to about 2% w/w.

4. The composition of claim 1, wherein the glycerin is present at a concentration of about 0.2% w/w to about 5% w/w.

5. The composition of claim 1, wherein the acrylates/C10-30 alkyl acrylate crosspolymer is present at a concentration of about 0.02% to about 0.5% w/w.

6. The composition of claim 1, wherein the castor oil is present at a concentration of about 0.05% to about 0.5% w/w.

7. The composition of claim 1, wherein the erythritol is present at a concentration of about 0.05% or about 3% w/w: and the levocarnitine is present at a concentration of about 0.05% or about 3% w/w.

8. The composition of claim 1, consisting of about 0.5% w/w polyoxyethylene (20) sorbitan monooleate, about 0.5% w/w carboxymethylcellulose sodium, about 1.0% w/w glycerin, about 0.6% w/w boric acid, about 0.1% w/w acrylates/C10-30 alkyl acrylate crosspolymer, about 0.25% w/w castor oil, about 0.25% w/w erythritol, about 0.25% w/w levocarnitine, sodium hydroxide, a pH of about 7.3 and water.

9. A method of treating, curing or mitigating dry eye syndrome comprising administering an effective amount of an ophthalmic composition according to claim 1 to an eye of a man or other animal in need thereof.

10. An ophthalmic composition consisting of polyoxyethylene (20) sorbitan monooleate, carboxymethylcellulose sodium, glycerin, boric acid, acrylates/C10-30 alkyl acrylate cross/golymer, castor oil, erythritol, levocarnitine, sodium hydroxide, a stabilized oxychloro complex and water.

11. The composition of claim 10, wherein the stabilized oxychloro complex is present at a concentration of about 0.002% to about 0.05% w/w.

12. The composition of claim 10, wherein the polyoxyethylene (20) sorbitan monooleate is present at a concentration of about 0.1% w/w to about 2% w/w.

13. The composition of claim 10, wherein the carboxymethylcellulose sodium is present at a concentration of about 0.1% w/w to about 2% w/w.

14. The composition of claim 10, wherein the glycerin is present at a concentration of about 0.2% w/w to about 5% w/w.

15. The composition of claim 10, wherein the acrylates/C10-30 alkyl acrylate crosspolymer is present at a concentration of about 0.02% to about 0.5% w/w.

16. The composition of claim 10, wherein the castor oil is present at a concentration of about 0.05% to about 0.5% w/w.

17. The composition of claim 10, wherein the erythritol is present at a concentration of about 0.05% or about 3% w/w; and the levocarnitine is present at a concentration of about 0.05% or about 3% w/w.

18. The composition of claim 10, consisting of about 0.5% w/w polyoxyethylene (20) sorbitan monooleate, about 0.5% w/w carboxymethylcellulose sodium, about 1.0% w/w glycerin, about 0.6% w/w boric acid, about 0.1% w/w acrylates/C10-30 alkyl acrylate crosspolymer, about 0.25% w/w castor oil, about 0.25% w/w erythritol, about 0.25% w/w levocarnitine, about 0.01% w/w stabilized oxychloro complex, sodium hydroxide, and water; and wherein the pH of the composition is about 7.3.

19. A method of treating, mitigating or curing dry eye syndrome comprising administering an effective amount of an ophthalmic composition according to claim 10 to an eye of a man or other animal in need thereof.

20. A method of treating, mitigating or curing dry eye syndrome comprising administering an effective amount of an ophthalmic composition according to claim 18 to an eye of a man or other animal in need thereof.

* * * * *

UNITED STATES PATENT AND TRADEMARK OFFICE
CERTIFICATE OF CORRECTION

PATENT NO.        : 8,957,048 B2
APPLICATION NO.   : 13/645035
DATED             : February 17, 2015
INVENTOR(S)       : Joseph G. Vehige et al.

It is certified that error appears in the above-identified patent and that said Letters Patent is hereby corrected as shown below:

On the title page, References cited, item (56), in column 2, under "Other Publications", line 16, delete "6115/2004," and insert -- 6/15/2004, --, therefor.

In the Specification

In column 3, line 22, delete "F-68from" and insert -- F-68 from --, therefor.

In column 3, line 26-27, delete "polyoxyethylenglyceroltriricinoleat" and insert -- polyoxyethyleneglyceroltriricinoleate --, therefor.

In column 3, line 40, delete "Pemulen™ Pemulen™" and insert -- Pemulen™, Pemulen™ --, therefor.

In column 6, line 14, delete "0.2% w/ w" and insert -- 0.2% w/w --, therefor.

In column 6, line 32, delete "(80)" and insert -- (20) --, therefor.

In column 6, line 46, delete "(80)" and insert -- (20) --, therefor.

In column 8, line 23, delete "erythrol," and insert -- erythritol, --, therefor.

In column 8, line 31, delete "erythrol," and insert -- erythritol, --, therefor.

In the Claims

In column 11, line 49, in claim 7, delete "w/w:" and insert -- w/w; --, therefor.

In column 12, line 12, in claim 10, delete "cross/golymer," and insert -- crosspolymer, --, therefor.

Signed and Sealed this
Thirtieth Day of June, 2015

Michelle K. Lee
*Director of the United States Patent and Trademark Office*